United States Patent
Bartholomaeus et al.

(10) Patent No.: US 6,576,260 B2
(45) Date of Patent: Jun. 10, 2003

(54) SUSTAINED-RELEASE FORM OF ADMINISTRATION CONTAINING TRAMADOL SACCHARINATE

(75) Inventors: Johannes Bartholomaeus, Aachen (DE); Heinrich Kugelmann, Aachen (DE); Iris Ziegler, Rott-Roetgen (DE)

(73) Assignee: Gruenenthal GmbH, Aachen (DE)

(*) Notice: Subject to any disclaimer, the term of this patent is extended or adjusted under 35 U.S.C. 154(b) by 0 days.

(21) Appl. No.: 10/084,248

(22) Filed: Feb. 28, 2002

(65) Prior Publication Data

US 2003/0035835 A1 Feb. 20, 2003

Related U.S. Application Data

(63) Continuation of application No. PCT/EP00/07527, filed on Aug. 3, 2000.

(30) Foreign Application Priority Data

Aug. 31, 1999 (DE) .......................... 199 40 740
Aug. 31, 1999 (DE) .......................... 199 40 944
May 16, 2000 (DE) .......................... 100 23 699

(51) Int. Cl.[7] .................. A61K 9/26; A61K 9/20; A61K 9/48; A61K 9/52; A61K 9/14
(52) U.S. Cl. .................. 424/469; 424/464; 424/465; 424/468; 424/470; 424/474; 424/475; 424/484; 424/486; 424/489; 424/451; 424/452; 424/457; 424/458; 424/460; 424/461; 424/462

(58) Field of Search ................. 424/464, 465, 424/468, 469, 470, 474, 475, 484, 486, 489, 451

(56) References Cited

U.S. PATENT DOCUMENTS

4,362,730 A * 12/1982 Rader et al. ............. 424/256
5,591,452 A * 1/1997 Miller et al. ............. 424/468
5,601,842 A * 2/1997 Bartholomaeus ......... 424/464
5,776,492 A * 7/1998 Betzing et al. ........... 424/465

FOREIGN PATENT DOCUMENTS

DE   19530575   7/1998
DE   19630035   9/1999

* cited by examiner

Primary Examiner—Thurman K. Page
Assistant Examiner—Rachel M. Bennett
(74) Attorney, Agent, or Firm—Crowell & Moring LLP

(57) ABSTRACT

Disclosed herein is sustained-release formulations of tramadol comprising tramadol sacchrinate coated with at least one sustained-release coating. The sustained release formulations may also contain tramadol in non-sustained release form, and other pharmaceutically acceptable excipients. Also disclosed are methods of preparation of and methods of treatment using the inventive formulations.

62 Claims, 4 Drawing Sheets

SUSTAINED-RELEASE FORM OF ADMINISTRATION CONTAINING TRAMADOL SACCHARINATE

CROSS REFERENCE TO RELATED APPLICATIONS

Figure 1:
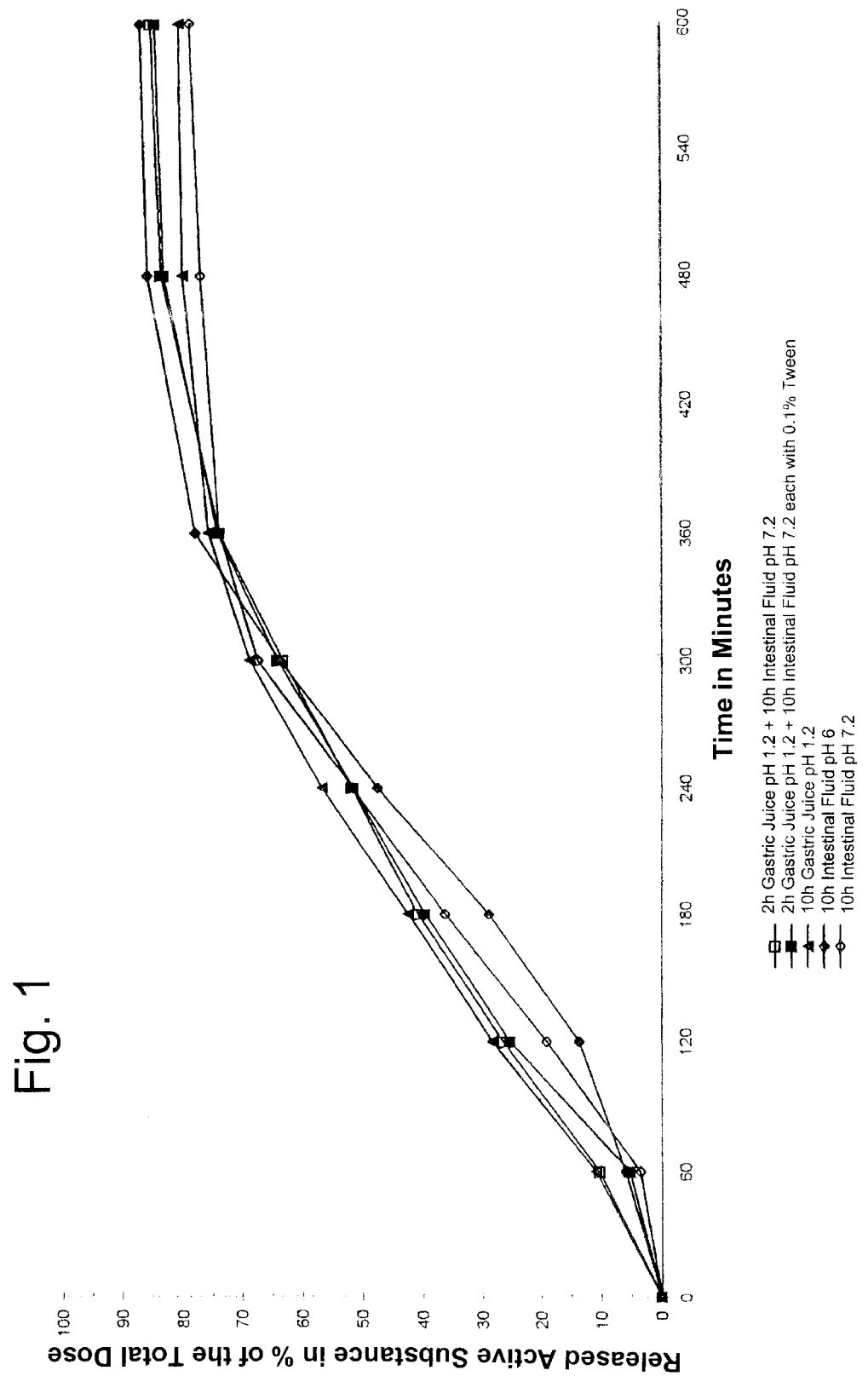

The present application is a continuation of international patent application no. PCT/EP00/07527, filed Aug. 3, 2000, designating the United States of America, the entire disclosure of which is incorporated herein by reference. Priority is claimed based on German patent application nos. 199 40 944.7, filed Aug. 31, 1999; 199 40 740.1, filed Aug. 31, 1999; and 100 23 699.5, filed May 16, 2000.

BACKGROUND OF THE INVENTION

The present invention relates to forms of administration of tramadol, retarded by a coating, which contain the active substance tramadol as tramadol saccharinate, optionally together with other auxiliary substances.

The very readily water-soluble tramadol hydrochloride—(1RS,2RS)-2-[(dimethylamino)methyl]-1-(3-methoxyphenyl)cyclohexanol hydrochloride—is often used for the control of intense and moderately intense pain.

The administration of tramadol hydrochloride in the form of sustained-release preparations represents a therapeutic improvement for this active substance. Even for this active substance with its relatively short half-life in the organism, retardation makes it possible to provide a preparation with a long-lasting action and also, through more constant blood levels, to reduce side effects and improve the patients' observance of the dosage instructions.

The active substance tramadol hydrochloride can be retarded e.g. by the application of sustained-release film coatings to pharmaceutical forms containing tramadol hydrochloride. However, retardation of this active substance with the aid of film coatings is relatively expensive because film coatings from aqueous coating systems for very readily water-soluble active substances of this kind frequently constitute an inadequate diffusion barrier and the permeability of these film coatings for tramadol hydrochloride usually changes during storage (P. B. O'Donnell, J. W. McGinity, "Mechanical Properties of Polymeric Films, Prepared from Aqueous Polymeric Dispersions in Aqueous Polymeric Coatings for Pharmaceutical Dosage Forms", Drugs and the Pharmaceutical Science, vol. 79, ed. J. W. McGinity, Marcel Decker, New York, Basle, Hong Kong 1997).

The manufacture of these retarded tramadol hydrochloride preparations therefore requires relatively expensive coating processes with multilayer films or time-consuming tempering processes, as described in U.S. Pat. Nos. 5,645,858, 5,580,578, 5,681,585 or U.S. Pat. No. 5,472,712, in K. Bauer, "Coated Pharmaceutical Dosage Forms", Medpharm Scientific Publishers, Stuttgart 1998, B. Sutter, Thesis, University of Düsseldorf, 1987, or in F. N. Christensen, Proceed. Intern. Symp. Contr. Rel. Bioact. Mater. 17, 124, 1990. If such coatings are applied from organic solvents, the associated environmental and solvent residue problems further increase the gcost of retarding tramadol hydrochloride.

SUMMARY AND DETAILED DESCRIPTION OF THE INVENTION

The object of the invention was therefore to provide a form of administration, or a pharmaceutical formulation, of the active substance tramadol, retarded with the aid of a coating, whose active substance release profile immediately after preparation is stable on storage without the need for laborious and expensive coating processes or time-consuming and hence cost-intensive tempering processes.

According to the invention, this object is achieved by the preparation of forms of administration, provided with a sustained-release coating, which contain the active substance tramadol as tramadol saccharinate, optionally together with other pharmaceutically acceptable auxiliary substances or excipients.

Surprisingly, the active substance release profile of the retarded forms of administration according to the invention immediately after preparation is stable on storage without the sustained-release coating having to undergo tempering after the conventional drying.

To prepare the tramadol saccharinate, tramadol—(1RS, 2RS)-2-[(dimethylamino)methyl]-1-(3-methoxyphenyl) cyclohexanol—and/or at least one appropriate, preferably water-soluble salt are reacted with saccharin and/or at least one, preferably water-soluble saccharin salt. The tramadol salt used is preferably tramadol hydrochloride and the saccharin salt used is preferably the sodium, potassium, calcium or ammonium salt and particularly preferably the sodium salt.

The tramadol saccharinate can also be formed in situ during the preparation of the forms of administration.

In terms of the present invention, in situ formation means that a readily water-soluble salt of tramadol is mixed with a water-soluble salt of saccharin, moistened and granulated several times, optionally extruded and/or formulated under some other energy input, preferably under pressure and/or with the application of heat.

For the in situ formation of tramadol saccharinate, the tramadol can be used as a water-soluble, pharmaceutically acceptable salt, preferably as tramadol hydrochloride, and the water-soluble, pharmaceutically acceptable salt of saccharin used is preferably the sodium, potassium, calcium or ammonium salt and particularly preferably the sodium salt.

The forms of administration according to the invention, provided with a sustained-release coating film, are preferentially suitable for oral administration.

In one preferred embodiment of the present invention, the forms of administration according to the invention are tablets, capsules or suspensions.

In another preferred embodiment of the present invention, the forms of administration according to the invention are multiparticulate, preferably in the form of microtablets, microcapsules, micropellets, granules, active substance crystals or pellets, optionally filled into capsules or compressed to tablets, or in a hydrophilic or lipophilic liquid, preferably as a homogeneous suspension, and particularly preferably in the form of juices or oral dispersions. If the forms of administration according to the invention are granules or pellets, they can preferably have a size in the range 0.1 to 3 mm and particularly preferably in the range 0.5 to 2 mm.

If the forms of administration according to the invention are microtablets, they can preferably have a diameter in the range 0.5 to 5 mm, particularly preferably in the range 1 to 3 mm and very particularly preferably in the range 1 to 2 mm.

If the forms of administration according to the invention are active substance crystals, microparticles, micropellets or microcapsules, they can preferably have a diameter in the range 10 μm to 1 mm, particularly preferably in the range 15 μm to 0.5 mm and very particularly preferably in the range 30 μm to 200 μm.

Depending on the embodiment, the forms of administration according to the invention can also contain, as additional constituents, the conventional auxiliary substances known to those skilled in the art.

If the forms of administration according to the invention are tablets or microtablets, they can preferably contain, as additional auxiliary substances, microcrystalline cellulose, cellulose ethers, lactose, starch and starch derivatives, sugar alcohols, calcium hydrogenphosphate and the conventional binders, flow regulators, lubricants and optionally disintegrants known to those skilled in the art.

If the forms of administration according to the invention are pellets, granules or micropellets, they can preferably contain, as additional auxiliary substances, microcrystalline cellulose, cellulose ethers, lactose, starch and starch derivatives, sugar alcohols, calcium hydrogenphosphate, fatty alcohols, glycerol esters or fatty acid esters.

If the forms of administration according to the invention are microcapsules or microparticles, they can contain the conventional auxiliary substances known to those skilled in the art, depending on the type of production process.

The various forms of administration according to the invention can be produced by different methods known to those skilled in the art.

If the form of administration according to the invention is tablets, they can be produced for example by the compression of granules produced by means of moist, dry or hot-melt granulation, or by direct tableting of the tramadol saccharinate, optionally with additional auxiliary substances. The tablets can also be produced by the compression of coated pellets, active substance crystals, microparticles or microcapsules.

The pellet form of administration according to the invention can be produced by extrusion and spheronization, by cumulative pelleting or by direct pelleting in a high-speed mixer or in a rotary fluidized bed. It is particularly preferred to produce the pellets by the extrusion of moist masses and subsequent spheronization.

Microcapsules are produced by conventional microencapsulation processes, e.g. by spray drying, spray congelation or coacervation.

In one preferred embodiment of the forms of administration according to the invention, the sustained-release coating film is preferably based on a water-insoluble, optionally modified, natural and/or synthetic polymer, on a natural, semisynthetic or synthetic wax, on a fat or fatty alcohol, or on a mixture of at least two of the above-mentioned components.

The water-insoluble polymers used to produce a sustained-release coating are preferably poly(meth)acrylates, particularly preferably poly($C_{1-4}$)alkyl (meth)acrylates, poly($C_{1-4}$)dialkylamino($C_{1-4}$)alkyl (meth)acrylates and/or copolymers thereof, and very particularly preferably copolymers of ethyl acrylate and methyl methacrylate with a monomer molar ratio of 2:1 (Eudragit NE30D®), copolymers of ethyl acrylate, methyl methacrylate and trimethylammonium ethyl methacrylate-chloride with a monomer molar ratio of 1:2:0.1 (Eudragit RS®), copolymers of ethyl acrylate, methyl methacrylate and trimethylammonium ethyl methacrylate-chloride with a monomer molar ratio of 1:2:0.2 (Eudragit RL®), or a mixture of at least two of the above-mentioned copolymers. These coating materials are commercially available as 30 wt. % aqueous latex dispersions, i.e. as Eudragit RS30D®, Eudragit NE30D® or Eudragit RL30D®, and are preferably also used as such for coating purposes.

Other preferred water-insoluble polymers which can be used to produce the sustained-release coating of the forms of administration according to the invention are polyvinyl acetates, optionally in combination with additional auxiliary substances. They are commercially available as an aqueous dispersion containing 27 wt. % of polyvinyl acetate, 2.5 wt. % of povidone and 0.3 wt. % of sodium laurylsulfate (Kollicoat SR 30 D®).

In another preferred embodiment, the sustained-release coatings of the forms of administration according to the invention are based on water-insoluble cellulose derivatives, preferably alkyl celluloses, e.g. ethyl cellulose, or cellulose esters, e.g. cellulose acetate. The ethyl cellulose or cellulose acetate coatings are preferably applied from aqueous pseudolatex dispersion. Aqueous ethyl cellulose pseudolatex dispersions are commercially available as 30 wt. % dispersions (Aquacoat®) or as 25 wt. % dispersions (Surelease®).

As natural, semisynthetic or synthetic waxes, fats or fatty alcohols, the sustained-release coating of the forms of administration according to the invention can preferably be based on carnauba wax, beeswax, glycerol monostearate, glycerol monobehenate (Compritol ATO888®), glycerol ditripalmitostearate (Precirol ATO5®), microcrystalline wax, cetyl alcohol, cetylstearyl alcohol or a mixture of at least two of these components.

If the sustained-release coating is based on a water-insoluble, optionally modified, natural and/or synthetic polymer, the coating dispersion or solution can contain, in addition to the appropriate polymer, a conventional, physiologically acceptable plasticizer known to those skilled in the art, in order to lower the required minimum film temperature.

Examples of suitable plasticizers are lipophilic diesters of a $C_6$–$C_{40}$ aliphatic or aromatic dicarboxylic acid and a $C_1$–$C_8$ aliphatic alcohol, e.g. dibutyl phthalate, diethyl phthalate, dibutyl sebacate or diethyl sebacate, hydrophilic or lipophilic citric acid esters, e.g. triethyl citrate, tributyl citrate, acetyltributyl citrate or acetyltriethyl citrate, polyethylene glycols, propylene glycol, glycerol esters, e.g. triacetin, Myvacet® (acetylated mono- and diglycerides, $C_{23}H_{44}O_5$ to $C_{25}H_{47}O_7$), medium-chain triglycerides Miglyol®), oleic acid or mixtures of at least two of said plasticizers.

Aqueous dispersions of Eudragit RS® and optionally Eudragit RL® preferably contain triethyl citrate.

The sustained-release coating of the form of administration according to the invention preferably contains the plasticizer(s) in amounts of 5 to 50 wt. %, particularly preferably 10 to 40 wt. % and very particularly preferably 10 to 30 wt. %, based on the amount of polymer(s) used. In individual cases, for example for cellulose acetate, it is also possible to use larger amounts of plasticizers, preferably of up to 110 wt. %.

The sustained-release coating can also contain other conventional auxiliary substances known to those skilled in the art, e.g. lubricants, preferably talcum or glycerol monostearate, coloured pigments, preferably iron oxides or titanium dioxide, or surfactants, e.g. Tween 80®.

The tramadol release profile obtained immediately after production of the form of administration according to the invention can be adjusted by the conventional methods known to those skilled in the art, e.g. by means of the thickness of the coating or by the use of additional auxiliary substances as constituents of the coating. Examples of suitable auxiliary substances are hydrophilic or pH-dependent pore-forming agents such as sodium carboxymethyl cellulose, cellulose acetate-phthalate, hydroxypropyl methyl cellulose acetate-succinate, lactose, polyethylene glycol or mannitol, or water-soluble polymers such as polyvinylpyrrolidone or water-soluble celluloses, preferably hydroxypropyl methyl cellulose or hydroxypropyl cellulose.

To further enhance the retardation, the sustained-release coating can also contain insoluble or lipophilic auxiliary substances such as alkylated silicon dioxide, which is marketed e.g. as Aerosil R972®, or magnesium stearate.

The forms of administration according to the invention for the release of tramadol saccharinate can additionally have an enteric coating which dissolves as a function of pH. Because of this coating, the forms of administration according to the invention can pass through the stomach undissolved and the tramadol saccharinate is only released in the intestinal tract. The enteric coating preferably dissolves at a pH of between 5 and 7.5.

The enteric coating is preferably based on methacrylic acid/methyl methacrylate copolymers with a monomer molar ratio of 1:1 (Eudragit L®), methacrylic acid/methyl methacrylate copolymers with a monomer molar ratio of 1:2 (Eudragit S®), methacrylic acid/ethyl acrylate copolymers with a monomer molar ratio of 1:1 (Eudragit L30D-55®), methacrylic acid/methyl acrylate/methyl methacrylate copolymers with a monomer molar ratio of 7:3:1 (Eudragit FS®), shellac, hydroxypropyl methyl cellulose acetate-succinates, cellulose acetate-phthalates or a mixture of at least two of these components, which can optionally also be used in combination with the above-mentioned water-insoluble poly(meth)acrylates, preferably in combination with Eudragit NE30D® and/or Eudragit RL® and/or Eudragit RS®.

The coatings of the form of administration according to the invention can be applied by the conventional processes known to those skilled in the art which are suitable for the particular coating, e.g. by the spraying of solutions, dispersions or suspensions, by the hot-melt process or by the powder application process. The solutions, dispersions or suspensions can be used in the form of aqueous or organic solutions or dispersions, preferably aqueous dispersions. Organic solvents which can be used are alcohols, for example ethanol or isopropanol, ketones, e.g. acetone, esters, for example ethyl acetate, and chlorinated hydrocarbons, e.g. dichloromethane, preference being given to alcohols and ketones. It is also possible to use mixtures of at least two of the above-mentioned solvents.

These processes are known from the state of the art, e.g. H. Sucker, Georg Thieme Verlag, 1991, pages 347 et seq. They are introduced here by way of reference and thus form part of the disclosure.

If the forms of administration according to the invention are multiparticulate, the sustained-release coating is preferably applied in such a way that, after preparation, the multiparticulate forms containing the tramadol saccharinate are coated with the appropriate polymers and optionally other auxiliary substances from aqueous and/or organic media, preferably from aqueous media, by the fluidized bed process, and the coating is preferably dried simultaneously at conventional temperatures in the fluidized bed without subsequently being tempered. In the case of poly(meth)acrylate coatings, the coating is preferably dried at an air inlet temperature in the range 30 to 50° C. and particularly preferably in the range 35 to 45° C.

In the case of coatings based on cellulose, e.g. ethyl cellulose or cellulose acetate, drying preferably takes place at a temperature in the range 50 to 80° C. and particularly preferably in the range 55 to 65° C.

Wax coatings can be applied by hot-melt coating in a fluidized bed and, after coating, cooled to complete the solidification at temperatures below the appropriate melting range. Wax coatings can also be applied by spraying solutions thereof in organic solvents.

For further modification of the active substance release profile, the sustained-release forms of administration according to the invention can also contain tramadol saccharinate in a sustained-release matrix, preferably as a uniform distribution.

Matrix materials which can be used are physiologically compatible, hydrophilic materials known to those skilled in the art. The hydrophilic matrix materials used are preferably polymers and particularly preferably cellulose ethers, cellulose esters and/or acrylic resins. The matrix materials used are very particularly preferably ethyl cellulose, hydroxypropyl methyl cellulose, hydroxypropyl cellulose, hydroxymethyl cellulose, poly(meth)acrylic acid and/or derivatives thereof such as their salts, amides or esters.

Other preferred matrix materials are those consisting of hydrophobic materials such as hydrophobic polymers, waxes, fats, long-chain fatty acids, fatty alcohols or corresponding esters or ethers, or mixtures thereof. The hydrophobic materials used are particularly preferably $C_{12}$–$C_{30}$ fatty acid mono- or diglycerides and/or $C_{12}$–$C_{30}$ fatty alcohols and/or waxes, or mixtures thereof.

It is also possible to use mixtures of the above-mentioned hydrophilic and hydrophobic materials as the sustained-release matrix material.

The sustained-release matrix can be prepared by the conventional methods known to those skilled in the art.

In another preferred embodiment, the forms of administration according to the invention contain the active substance tramadol not only in its retarded form but also in its non-retarded form, e.g. as tramadol hydrochloride. By combination with the immediately released active substance, a high initial dose can be achieved for the rapid alleviation of pain. The slow release from the retarded form then prevents the analgesic effect from diminishing.

The amount of tramadol to be administered to the patient varies e.g. as a function of the patient's weight, the indication and the degree of severity of the pain or disease. The amount of tramadol to be administered, and its release, are preferably adjusted so that it has to be taken at most twice a day and preferably only once a day.

If taken once a day, the forms of administration according to the invention preferably contain 10 to 1200 mg, particularly preferably 20 to 1000 mg and very particularly preferably 100 to 800 mg of tramadol.

If taken twice a day, the forms of administration according to the invention preferably contain 5 to 600 mg, particularly preferably 10 to 500 mg and very particularly preferably 50 to 400 mg of tramadol.

The forms of administration according to the invention can preferably be used for the control of pain or for the treatment of urinary incontinence, coughs, inflammatory reactions, allergic reactions, depression, drug abuse, alcohol abuse, gastritis, diarrhoea, cardiovascular disease, respiratory disease, mental illness or epilepsy, and particularly preferably for the control of pain or for the treatment of urinary incontinence or coughs.

The forms of administration according to the invention have the advantage that, immediately after preparation, their active substance release profile is stable on storage without the need for tempering, which normally follows drying, or for an expensive coating process. This makes it possible to reduce the production time and hence also the costs of producing the forms of administration according to the invention.

Furthermore, the release of the active substance tramadol from the forms of administration according to the invention, provided with a sustained-release coating applied from an aqueous medium, is surprisingly retarded far more than from the forms of administration, provided with a sustained-release coating of identical composition, which contain the active substance tramadol as tramadol hydrochloride. Application of the sustained-release coating film from an aqueous medium has the further advantage that the expensive recovery or organic solvents is not necessary and that the forms of administration according to the invention no longer contain solvent residues.

A further feature of the forms of administration according to the invention is that the release of the active substance tramadol therefrom is not affected by varying the release conditions within the conventional framework, e.g. by means of the ion concentrations of the buffers, the presence of surface-active substances or the application of different mechanical stresses.

The release profiles of the forms of administration according to the invention were determined as follows:

The form of administration according to the invention was tested in a cage apparatus or in a paddle stirrer, as described in the European Pharmacopoeia, at a release medium temperature of 37±0.5° C. and a speed of rotation of 100 rpm or 50 rpm in the case of the paddle stirrer, for 2 hours, in 600 ml of artificial gastric juice at pH 1.2. The form of administration was then tested for a further 8 hours in 900 ml of artificial intestinal juice at pH 7.2. The amount of tramadol saccharinate released at any given time was determined by HPLC. The values shown have been averaged over 3 samples in each case.

The invention is illustrated below with the aid of Examples 1 to 11. These illustrations are given solely by way of example and do not limit the general spirit of the invention.

EXAMPLES

Example 1

To prepare tramadol saccharinate, equimolar amounts of tramadol hydrochloride—(1RS,2RS)-2-[(dimethylamino) methyl]-1-(3-methoxyphenyl)cyclohexanol hydrochloride—and saccharin sodium or saccharin sodium dihydrate are each completely dissolved in the minimum amount of water, with heating. The two solutions are then mixed together, with stirring. On cooling, the tramadol saccharinate crystallizes out of the aqueous solution after only a short time and is isolated by conventional methods and purified with ethanol.

Preparation of Pellets 2500 g of tramadol saccharinate and 2500 g of microcrystalline cellulose (Avicel PH 105®, FMC) are mixed for 10 minutes in a Diosna P25 high-speed mixer and then granulated for 10 minutes with 3300 g of demineralized water. The moist granules are extruded in a NICA E140 extruder with a 1.0×2.0 mm extrusion die and the moist extrudate is spheronized in 2.7 kg batches in a NICA spheronizer for 15 minutes at 800 rpm. The pellets are then dried overnight at 50° C. in a drying cabinet. The yield of pellets with a particle size in the range 800 to 1250 µm is over 90%.

Application of the Coating 3 kg of these pellets (800–1250 µm) are coated in a fluidized bed (Hüttlin HKC05) with an aqueous dispersion of the following composition, at a product temperature of 26 to 30° C., until the weight has increased by 16% (based on the weight of the starting pellets). This coating application corresponds to a polymer application of 13 wt. % (based on the weight of the starting pellets). The pellets are then dried for 10 minutes in the fluidized bed at 45° C.

Aqueous Dispersion for 3 kg of Pellets

| | |
|---|---:|
| Eudragit RS 30 D ® | 1049.0 g |
| Eudragit RL 30 D ® | 296.0 g |
| Triethyl citrate | 80.7 g |
| Glycerol monostearate | 20.2 g |
| Tween 80 ® | 1.9 g |
| Demineralized water | 1074.2 g |
| Total: | 2522.0 g |

345 mg of pellets provided with a sustained-release coating contain 149 mg of tramadol saccharinate, corresponding to 100 mg of the active substance tramadol hydrochloride.

The release profile was determined in a cage apparatus by the method indicated above and is shown in Table 1 below and in FIG. 3.

TABLE 1

| Time (min) | Tramadol saccharinate released in % of the total dose of active substance |
|---:|---:|
| 0 | 0 |
| 60 | 11 |
| 120 | 32 |
| 180 | 46 |
| 240 | 57 |
| 300 | 67 |
| 360 | 76 |
| 480 | 93 |
| 600 | 105 |

The active substance release from the pellets produced in this way, provided with a sustained-release coating, was also tested, by the method indicated above, in release media of different composition according to Table 2 below:

TABLE 2

| | |
|---|---|
| a) | 2 hours in gastric juice at pH 1.2 and 10 hours in intestinal juice at pH 7.2 |
| b) | 10 hours in gastric juice at pH 1.2 |
| c) | 10 hours in intestinal juice at pH 6.0 |
| d) | 10 hours in intestinal juice at pH 7.2 |
| e) | 2 hours in gastric juice at pH 1.2 and 10 hours in intestinal juice at pH 7.2 with 0.1% of Tween 80 ® in each case |

The results of these experiments are shown in FIG. 1, where it can be seen that the release profile of the tramadol saccharinate pellets provided with a sustained-release coating is barely affected by the change in composition of the release medium. Neither the pH, nor the ionic strength, nor the presence of surface-active substances affects the release profile of the pellets provided with the sustained-release coating.

Comparative Example 1

Preparation of Pellets Containing Tramadol Hydrochloride 275 g of tramadol hydrochloride, 75 g of microcrystalline cellulose (Avicel PH 105®, FMC) and 150 g of hydroxypropyl cellulose with a low degree of substitution (1-HPC LH31®) are mixed for 10 minutes in a Kenwood Chef planetary mixer and then granulated for 10 minutes with 250 g of demineralized water. The moist granules are extruded in a NICA E140 extruder with a 1.0×2.0 mm extrusion die and the moist extrudate is spheronized in a NICA spheronizer for 15 minutes at 800 rpm. The pellets are then dried overnight at 50° C. in a drying cabinet. The yield of pellets with a particle size in the range 800 to 1250 µm is over 90%.

Application of the Coating 320 g of these pellets (800–1250 µm) were coated in a fluidized bed (Aeromatic, Strea 1) with an aqueous dispersion of the following composition, at a product temperature of 26 to 32° C., until the weight had increased by 25% (based on the weight of the starting pellets). This coating application corresponds to a polymer application of 16 wt. % (based on the weight of the starting pellets). The pellets are then dried for 10 minutes in the fluidized bed at 45° C.

Aqueous Dispersion for 320 g of Pellets

| | |
|---|---|
| Eudragit RS 30 D ® | 152.8 g |
| Eudragit RL 30 D ® | 13.9 g |
| Triethyl citrate | 15.0 g |
| Talcum | 15.0 g |
| Demineralized water | 203.3 g |
| Total: | 400.0 g |

228 mg of pellets provided with a sustained-release coating contain 100 mg of tramadol hydrochloride.

The release profile was determined in a cage apparatus by the method indicated above. The results of these experiments and of those for the pellets of Example 1 according to the invention are shown in FIG. 4.

Figure 4:
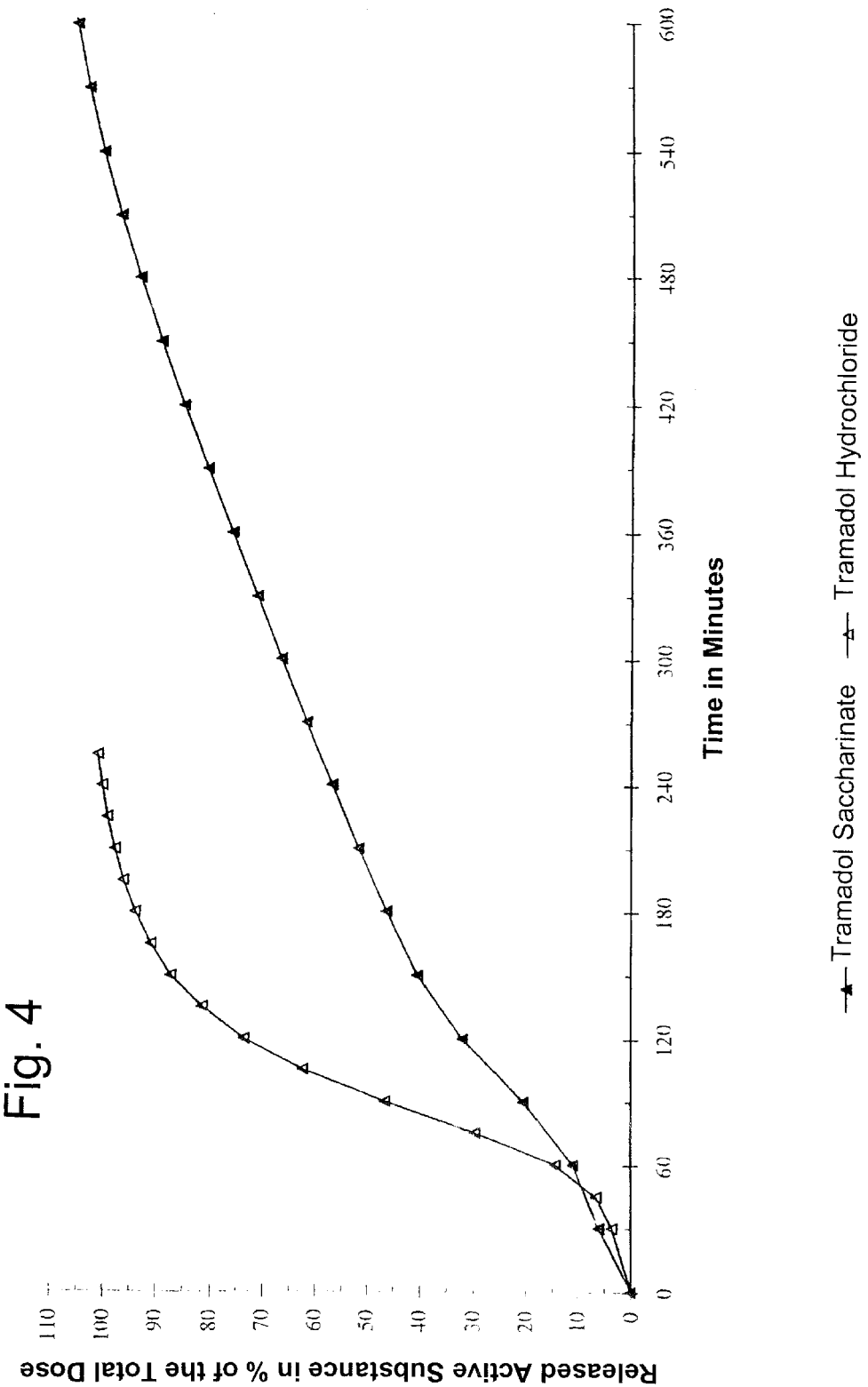

As can be seen from FIG. 4, the tramadol saccharinate pellets provided with a sustained-release coating exhibit active substance release over 10 hours, whereas, after a short delay, the tramadol hydrochloride pellets provided with a sustained-release coating release the active substance almost completely within only 4 hours, despite the thicker polymer coating and the less permeable polymer composition of the coating.

The intrinsic release of the active substances tramadol hydrochloride and tramadol saccharinate was also determined.

The intrinsic active substance release is determined for both tramadol hydrochloride and tramadol saccharinate in demineralized water (37° C.±0.5° C.) using the method "<1087>intrinsic dissolution" published in USP 24-NF19 first supplement (pp. 2706 et seq.). The intrinsic release of each of the two active substances is calculated from the gradient of the cumulative active substance release up to and including the time at which 10% of the pellets have been released. It is given below as the release rate in mg·min$^{-1}$·cm$^{-2}$.

Intrinsic Release in Water

| | |
|---|---|
| Tramadol hydrochloride: | 21 mg · min$^{-1}$ · cm$^{-2}$ |
| Tramadol saccharinate: | 2 mg · min$^{-1}$ · cm$^{-2}$ |

The difference in the intrinsic active substance release clearly shows that tramadol saccharinate is released from pharmaceutical forms considerably more slowly than tramadol hydrochloride and therefore also permeates diffusion barriers more slowly.

Example 2

Preparation of Pellets 505 g of tramadol saccharinate and 505 g of microcrystalline cellulose (Avicel PH 105®, FMC) are mixed for 10 minutes in a Kenwood Chef planetary mixer and then granulated for 10 minutes with 630 g of demineralized water. The moist granules are extruded in a NICA E140 extruder with a 1.0×2.0 mm extrusion die and the moist extrudate is spheronized in a NICA spheronizer for 15 minutes at 800 rpm. The pellets are then dried overnight at 50° C. in a drying cabinet. The yield of pellets with a particle size in the range 800 to 1250 µm is over 90%.

Application of the Coating 200 g of these pellets (800–1250 µm) are coated in a fluidized bed (Aeromatic, Strea 1) with an aqueous dispersion of the following composition, at a product temperature of 26 to 30° C., until the weight has increased by 27% (based on the weight of the starting pellets). This coating corresponds to a polymer application of 21 wt. % (based on the weight of the starting pellets). The coated pellets are then dried for 10 minutes in the fluidized bed at 45° C.

Aqueous Dispersion for 200 g of Pellets

| | |
|---|---|
| Eudragit RS 30 D ® | 108.6 g |
| Eudragit RL 30 D ® | 30.6 g |
| Triethyl citrate | 8.3 g |
| Glycerol monostearate | 2.1 g |
| Tween 80 ® | 0.2 g |
| Demineralized water | 111.2 g |
| Total: | 261.0 g |

379 mg of pellets provided with a sustained-release coating contain 149 mg of tramadol saccharinate, corresponding to 100 mg of the active substance tramadol hydrochloride.

The release profile was determined in a cage apparatus by the method described above and is shown in Table 3 below and in FIG. 3. As a departure from the conditions described above, the coated pellets were tested for 10 hours in artificial intestinal juice at pH 7.2.

TABLE 3

| Time (min) | Tramadol saccharinate released in % of the total dose of active substance |
|---|---|
| 0 | 0 |
| 60 | 3 |
| 120 | 14 |
| 180 | 26 |
| 240 | 35 |
| 300 | 46 |
| 360 | 56 |
| 480 | 74 |
| 600 | 91 |
| 720 | 100 |

Example 3

Preparation of Pellets 505 g of tramadol saccharinate and 505 g of microcrystalline cellulose (Avicel PH 105®, FMC) are mixed for 10 minutes in a Kenwood Chef planetary mixer and then granulated for 10 minutes with 630 g of demineralized water. The moist granules are extruded in a NICA E140 extruder with a 1.0×2.0 mm extrusion die and the moist extrudate is spheronized in a NICA spheronizer for 15 minutes at 800 rpm. The pellets are then dried overnight at 50° C. in a drying cabinet. The yield of pellets with a particle size in the range 800 to 1250 μm is over 90%.

Application of the Coating 200 g of these pellets (800–1250 μm) are coated in a fluidized bed (Aeromatic, Strea 1) with an aqueous dispersion of the following composition, at a product temperature of 26 to 30° C., until the weight has increased by 21% (based on the weight of the starting pellets). This coating application corresponds to a polymer application of 14 wt. % (based on the weight of the starting pellets). The coated pellets are subjected to the release test either directly after coating and conventional drying or after tempering at 40° C. for 15 hours in a drying cabinet.

Aqueous Dispersion for 200 g of Pellets

| | |
|---|---|
| Eudragit RS 30 D ® | 80.0 g |
| Eudragit RL 30 D ® | 20.0 g |
| Triethyl citrate | 6.0 g |
| Talcum | 6.0 g |
| Demineralized water | 88.0 g |
| Total: | 200.0 g |

361 mg of pellets provided with a sustained-release coating contain 149 mg of tramadol saccharinate, corresponding to 100 mg of the active substance tramadol hydrochloride.

The release profiles were determined in each case in a cage apparatus by the method described above and are shown in Table 4 below and, for the non-tempered pellets, in FIG. 3.

TABLE 4

| Time (min) | Tramadol saccharinate released in % of the total dose of active substance without tempering | Tramadol saccharinate released in % of the total dose of active substance 15 h tempering at 40° C. |
|---|---|---|
| 0 | 0 | 0 |
| 60 | 16 | 15 |
| 120 | 29 | 27 |
| 180 | 37 | 34 |
| 240 | 45 | 41 |
| 360 | 63 | 57 |
| 480 | 79 | 73 |
| 600 | 92 | 87 |

The differences of approx. 5% between the values for the active substance release without and with tempering correspond to the usual scatter of experimental values, so tempering after application of the coating has no effect on the release profile.

Example 4

Preparation of Pellets 252.5 g of tramadol saccharinate and 252.5 g of microcrystalline cellulose (Avicel PH 105®, FMC) are mixed for 10 minutes in a Kenwood Chef planetary mixer and then granulated for 10 minutes with 338.0 g of demineralized water. The moist granules are extruded in a NICA E140 extruder with a 1.0×2.0 mm extrusion die and the moist extrudate is spheronized in a NICA spheronizer for 15 minutes at 800 rpm. The pellets are then dried overnight at 50° C. in a drying cabinet. The yield of pellets with a particle size in the range 800 to 1250 μm is over 90%.

Application of the Coating 170 g of these pellets (800–1250 μm) are coated in a fluidized bed (Aeromatic, Strea 1) with an aqueous dispersion of the following composition, at a product temperature of 26 to 30° C., until the weight has increased by 28% (based on the weight of the starting pellets). This coating application corresponds to a polymer application of 20 wt. % (based on the weight of the starting pellets). The coated pellets are then dried for 10 minutes in the fluidized bed at 45° C.

Aqueous Dispersion for 170 g of Pellets

| | |
|---|---|
| Eudragit RS 30 D ® | 68.1 g |
| Eudragit RL 30 D ® | 45.4 g |
| Triethyl citrate | 6.8 g |
| Talcum | 6.8 g |
| Demineralized water | 99.9 g |
| Total: | 227.0 g |

381 mg of pellets provided with a sustained-release coating contain 149 mg of tramadol saccharinate, corresponding to 100 mg of the active substance tramadol hydrochloride.

The release profile was determined in a cage apparatus by the method indicated above and is shown in Table 5 below and in FIG. 3. As a departure from the conditions described above, the coated pellets were tested for 6 hours in artificial intestinal juice at pH 7.2.

TABLE 5

| Time (min) | Tramadol saccharinate released in % of the total dose of active substance |
|---|---|
| 0 | 0 |
| 30 | 4 |
| 120 | 62 |
| 240 | 94 |
| 300 | 99 |
| 480 | 100 |

Example 5

Preparation of Pellets 505.0 g of tramadol saccharinate and 505.0 g of microcrystalline cellulose (Avicel PH 105®, FMC) are mixed for 10 minutes in a Kenwood Chef planetary mixer and then granulated for 10 minutes with 630.0 g of demineralized water. The moist granules are extruded in a NICA E140 extruder with a 1.0×2.0 mm extrusion die and the moist extrudate is spheronized in a NICA spheronizer for 15 minutes at 800 rpm. The pellets are then dried overnight 50° C. in a drying cabinet. The yield of pellets with a particle size in the range 800 to 1250 μm is over 90%.

Application of the Coating 200 g of these pellets (800–1250 μm) are coated in a fluidized bed (Aeromatic, Strea 1) with an aqueous dispersion of the following composition, at a product temperature of 26 to 30° C., until the weight has increased by 20% (based on the weight of the starting pellets). This coating application corresponds to a polymer application of 16 wt. % (based on the weight of the starting pellets). The coated pellets are then dried for 10 minutes in the fluidized bed at 45° C.

Aqueous Dispersion for 200 g of Pellets

| | |
|---|---|
| Eudragit RS 30 D ® | 106.1 g |
| Triethyl citrate | 6.4 g |
| Glycerol monostearate | 1.6 g |

| -continued | |
|---|---|
| Tween 80 ® | 0.2 g |
| Demineralized water | 84.7 g |
| Total: | 199.0 g |

358 mg of pellets provided with a sustained-release coating contain 149 mg of tramadol saccharinate, corresponding to 100 mg of the active substance tramadol hydrochloride.

The release profile was determined in a cage apparatus by the method indicated above and is shown in Table 6 below and in FIG. 3. As a departure from the conditions described above, the coated pellets were tested for 14 hours in artificial intestinal juice at pH 7.2.

TABLE 6

| Time (min) | Tramadol saccharinate released in % of the total dose of active substance |
|---|---|
| 0 | 0 |
| 60 | 0 |
| 120 | 0 |
| 180 | 0 |
| 240 | 2 |
| 300 | 3 |
| 360 | 5 |
| 420 | 7 |
| 480 | 8 |
| 600 | 10 |
| 720 | 12 |
| 840 | 14 |
| 960 | 15 |

Example 6

Testing of the storage stability of tramadol saccharinate pellets provided with a sustained-release coating:

The pellets prepared according to Example 1, provided with a sustained-release coating, were stored in closed glass vessels for 1 week or 2 weeks, either at 30° C. and 70% relative humidity, or at 40° C. dry, or at 40° C. and 75% relative humidity, and in each case the release profile was determined, after storage, by the method described above. As a departure from the conditions described above, the coated pellets were tested for 10 hours in artificial intestinal juice at pH 7.2.

Figure 2:
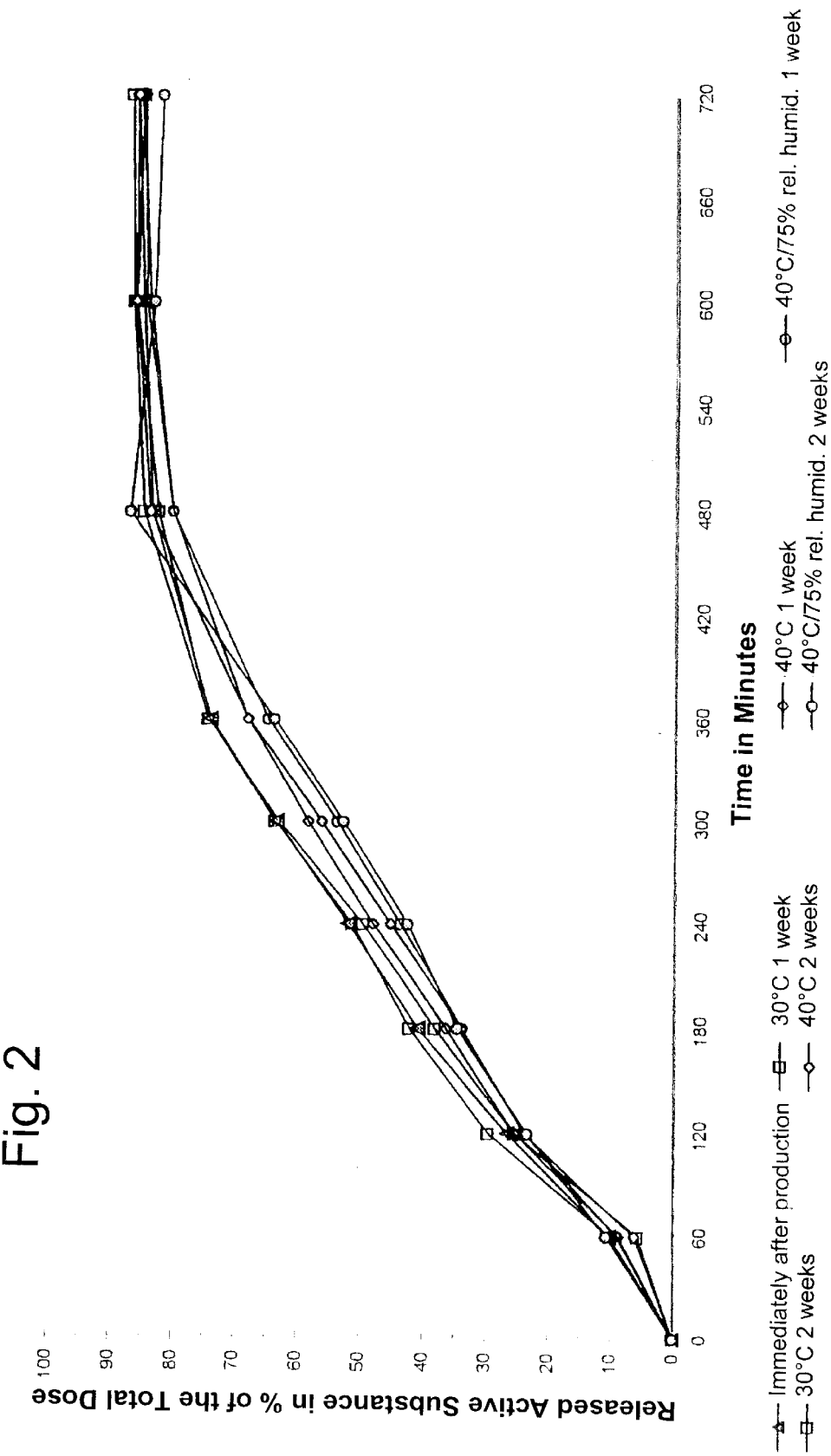

The results of these experiments are shown in FIG. 2, where it can be seen that storage at 30° C. and 70% relative humidity, and at 40° C. dry, has no effect whatsoever on the active substance release profile. Even after storage at 40° C. and 75% relative humidity, release from the partially agglutinated pellets is only slowed down very slightly. Immediately after preparation, the forms of administration of tramadol saccharinate according to the invention therefore exhibit a retarded release profile of the active substance which is stable on storage without tempering.

Example 7
Preparation of Pellets 250 g of tramadol saccharinate and 250 g of microcrystalline cellulose (Avicel PH 105®) are mixed for 10 minutes in a Kenwood Chef planetary mixer and then granulated for 10 minutes with 443 g of demineralized water. The moist granules are extruded in a NICA E140 extruder with a 1.0×2.0 mm extrusion die and the moist extrudate is then spheronized in a NICA spheronizer for 15 minutes at 800 rpm. The pellets are then dried overnight at 50° C. in a drying cabinet. The yield of pellets with a particle size in the range 800 to 1250 µm is over 90%.

Application of the Coating 170 g of these pellets (800–1250 µm) are coated in a fluidized bed (Aeromatic, Strea 1) with an aqueous dispersion of the following composition, at a product temperature of 35 to 40° C., until the weight has increased by 5% (based on the weight of the starting pellets). The coated pellets are then dried for two hours at 60° C. in a drying cabinet.

Aqueous Dispersion for 170 g of Pellets

| Surelease E-7-7050 ®* | 34.0 g |
|---|---|
| Demineralized water | 23.0 g |
| Total: | 57.0 g |

*25% aqueous ethyl cellulose pseudolatex dispersion. The commercially available ready-to-use dispersion contains dibutyl sebacate as plasticizer and silicon dioxide as lubricant.

313 mg of pellets provided with a sustained-release coating contain 149 mg of tramadol saccharinate, corresponding to a dose of 100 mg of tramadol hydrochloride.

The release profile was determined in a cage apparatus by the method indicated above and is shown in Table 7 below and in FIG. 3.

TABLE 7

| Time (min) | Tramadol saccharinate released in % of the total dose of active substance |
|---|---|
| 0 | 0 |
| 30 | 15 |
| 120 | 58 |
| 240 | 69 |
| 300 | 71 |
| 480 | 76 |
| 600 | 79 |

Example 8
Preparation of Tablets
Composition per Tablets

| Tramadol saccharinate | 149 mg |
|---|---|
| Cellactose | 146 mg |
| Magnesium stearate | 3 mg |

The Cellactose and the magnesium stearate are sieved and then homogeneously mixed with the tramadol saccharinate for 10 minutes in a tumbling mixer (Bohle, LM 40). This mixture is compressed on a Korsch EKO eccentric press with a die to give 10 mm dragee-shaped tablets with a height of approx. 5 mm and a radius of curvature of 8 mm.

Application of the Coating 2000 of these tablets are coated in a fluidized bed (Aeromatic, Strea 1) with an aqueous dispersion of the following composition, at a product temperature of 26 to 30° C., until the weight has increased by 6.5 wt. % (based on the weight of the starting tablet). This coating application corresponds to a polymer application of 5.0 wt. % (based on the weight of the starting tablet). The coated tablets are dried for 10 minutes at 40° C. in a drying cabinet.

Aqueous Dispersion for 2000 Tablets

| | |
|---|---|
| Eudragit RS 30 D ® | 69.7 g |
| Eudragit RL 30 D ® | 29.8 g |
| Triethyl citrate | 6.0 g |
| Glycerol monostearate | 1.5 g |
| Tween 80 ® | 0.1 g |
| Demineralized water | 92.4 g |
| Total: | 199.5 g |

The release profile was determined in a paddle stirrer by the method indicated above and is shown in Table 8 below.

Comparative Example 2
Preparation of Tablets
Composition per Tablet

| | |
|---|---|
| Tramadol hydrochloride | 100 mg |
| Cellactose | 98 mg |
| Magnesium stearate | 2 mg |

The Cellactose and the magnesium stearate are sieved and then homogeneously mixed with the tramadol hydrochloride for 10 minutes in a tumbling mixer (Bohle, LM 40). This mixture is compressed on a Korsch EK0 eccentric press with a die to give 9 mm dragee-shaped tablets with a height of approx. 5 mm and a radius of curvature of 8 mm.

Application of the Coating 2000 of these tablets are coated in a fluidized bed (Aeromatic, Strea 1) with an aqueous dispersion of the following composition, at a product temperature of 26 to 30° C., until the weight has increased by 6.5% (based on the weight of the starting tablet). This coating application corresponds to a polymer application of 5.0 wt. % (based on the weight of the starting tablet). The coated tablets are dried for 10 minutes at 40° C. in a drying cabinet.

Aqueous Dispersion for 2985 Tablets

| | |
|---|---|
| Eudragit RS 30 D ® | 69.7 g |
| Eudragit RL 30 D ® | 29.8 g |
| Triethyl citrate | 6.0 g |
| Glycerol monostearate | 1.5 g |
| Tween 80 ® | 0.1 g |
| Demineralized water | 92.4 g |
| Total: | 199.5 g |

The release profile was determined in a paddle stirrer by the method indicated above and is shown in Table 8 below.

TABLE 8

| Time (min) | Tramadol saccharinate released in % of the total dose of active substance | Tramadol hydrochloride released in % of the total dose of active substance |
|---|---|---|
| 0 | 0 | 0 |
| 30 | 1 | 2 |
| 240 | 9 | 91 |
| 480 | 17 | 96 |
| 720 | 25 | 98 |

Whereas >90% of the active substance tramadol hydrochloride has already been released from the coated tablets within 4 hours, tramadol saccharinate is released from the coated tablets considerably more slowly and at a constant rate, only 25% of the total dose having been released after 12 hours.

Here again it is clear that the slower rate of dissolution of tramadol saccharinate with identical diffusion barriers results in a greater retardation than in the case of tramadol hydrochloride and, in contrast to the latter, results in zero-order release kinetics even with smaller film layer thicknesses.

Example 9
Preparation of Pellets 500 g of tramadol hydrochloride, 345 g of sodium saccharinate and 845 g of microcrystalline cellulose (Avicel PH 101®) are mixed for 10 minutes and then granulated for 10 minutes with a sufficient amount of demineralized water for the purpose. After granulation, the granules are extruded in a Nica E140 extruder with a 0.8×1.6 mm extrusion die and the extrudate is granulated again with a sufficient amount of water to give a plastic mass. This is extruded again. The moist extrudate is spheronized in a Nica type S450 spheronizer. After drying in a drying cabinet, the pellets are graded, >90% of the pellets having a size in the range 0.63 to 1.0 mm.

Application of the Coatings 1000 g of these pellets are coated in a fluidized bed (Hüttlin HKC05) with an aqueous dispersion of the following composition, at a product temperature of 26 to 30° C., until the weight has increased by 20% (based on the weight of the starting pellets). This coating application corresponds to a polymer application of 16 wt. % (based on the weight of the starting pellets). The pellets are then dried for 10 minutes in the fluidized bed at 45° C.

Aqueous Dispersion for 1000 g of Pellets

| | |
|---|---|
| Eudragit RS 30 D ® | 499.5 g |
| Eudragit RL 30 D ® | 166.5 g |
| Triethyl citrate | 40.0 g |
| Glycerol monostearate | 10.0 g |
| Tween 80 ® | 1.1 g |
| Demineralized water | 612.9 g |
| Total: | 1330 g |

Filling of the Coated Pellets into Capsules 406 mg of the pellets provided with a sustained-release coating (corresponding to a content of 100 mg of the active substance tramadol hydrochloride) are filled into size 0 hard gelatin capsules on a Zanasi E6 encapsulating machine.

The release profile was determined in a cage apparatus by the method indicated above and is shown in Table 9 below and in FIG. 3. As a departure from the conditions described above, the coated pellets were tested for 10 hours intestinal juice at pH 7.2.

TABLE 9

| Time in min | Tramadol saccharinate released in % of the total dose of active substance |
|---|---|
| 0 | 0 |
| 60 | 7 |
| 120 | 22 |
| 240 | 53 |
| 480 | 91 |
| 600 | 99 |
| 720 | 100 |

Example 10

The pellets are prepared according to Example 4.

400 g of these pellets (800–1250 μm) are coated in a fluidized bed (Aeromatic, Strea 1) with an aqueous dispersion of the following composition, at a product temperature of 26 to 30° C., until the weight has increased by 25% (based on the weight of the starting pellets). This coating application corresponds to a polymer application of 20 wt. % (based on the weight of the starting pellets). The coated pellets are dried for 10 minutes at 40° C. in the fluidized bed apparatus.
Aqueous Dispersion for 400 g of Pellets

| | |
|---|---|
| Eudragit RS 30 D ® | 200.0 g |
| Eudragit RL 30 D ® | 66.7 g |
| Triethyl citrate | 16.0 g |
| Glycerol monostearate | 4.0 g |
| Tween 80 ® | 0.5 g |
| Demineralized water | 212.8 g |
| Total: | 500.0 g |

373 mg of pellets provided with a sustained-release coating contain 149 mg of tramadol saccharinate, corresponding to a dose of 100 mg of tramadol hydrochloride.
Preparation of Tablets
Composition per Tablet

| | |
|---|---|
| Coated pellets | 373 mg |
| Kollidon CL ® | 22.4 mg |
| Avicel PH 101 ® | 142.0 mg |
| Magnesium stearate | 2.6 mg |
| Total: | 540 mg |

The pellets provided with a sustained-release coating are mixed for 5 minutes in a tumbling mixer (Bohle, LM 40) with Kollidon CL® (crosslinked polyvinylpyrrolidone) and then mixed for a further 10 minutes with microcrystalline cellulose (Avicel PH 101®) and magnesium stearate. This mixture is compressed on a rotary tablet press (Fette, P1200) to round, biplanar tablets each weighing 500 mg, with a diameter of 12 mm and a hardness of 100 to 130 N.

In an aqueous medium, these tablets disintegrate into the individual pellets within 1–2 minutes.

The release profile was determined in a paddle stirrer by the method described above and is shown in Table 10 below and in FIG. 3.

TABLE 10

| Time (min) | Tramadol saccharinate released in % of the total dose of active substance |
|---|---|
| 0 | 0 |
| 30 | 8 |
| 120 | 22 |
| 240 | 46 |
| 300 | 57 |
| 480 | 86 |
| 600 | 102 |

Example 11

The pellets are prepared according to Example 2.

200 g of these pellets (800–1250 μm) are coated in a fluidized bed (Aeromatic, Strea 1) with an aqueous dispersion of the following composition, at a product temperature of 35 to 40° C., until the weight has increased by 20% (based on the weight of the starting pellets). This coating application corresponds to a polymer application of 15 wt. % (based on the weight of the starting pellets). The coated pellets are dried for 10 minutes at 45° C. in the fluidized bed apparatus.
Aqueous Dispersion for 200 g of Pellets

| | |
|---|---|
| Kollicoat ® RS 30 D | 100.0 g |
| Propylene glycol | 3.0 g |
| Talcum | 7.0 g |
| Demineralized water | 90.0 g |
| Total: | 200.0 g |

358 mg of pellets provided with a sustained-release coating contain 149 mg of tramadol saccharinate, corresponding to a dose of 100 mg of tramadol hydrochloride.

The release profile was determined in a cage apparatus by the method indicated above and is shown in Table 11 below.

TABLE 11

| Time (min) | Tramadol saccharinate released in % of the total dose of active substance |
|---|---|
| 0 | 0 |
| 30 | 6 |
| 120 | 37 |
| 180 | 54 |
| 240 | 61 |
| 300 | 71 |
| 480 | 76 |
| 600 | 92 |
| 720 | 98 |

Figure 3:
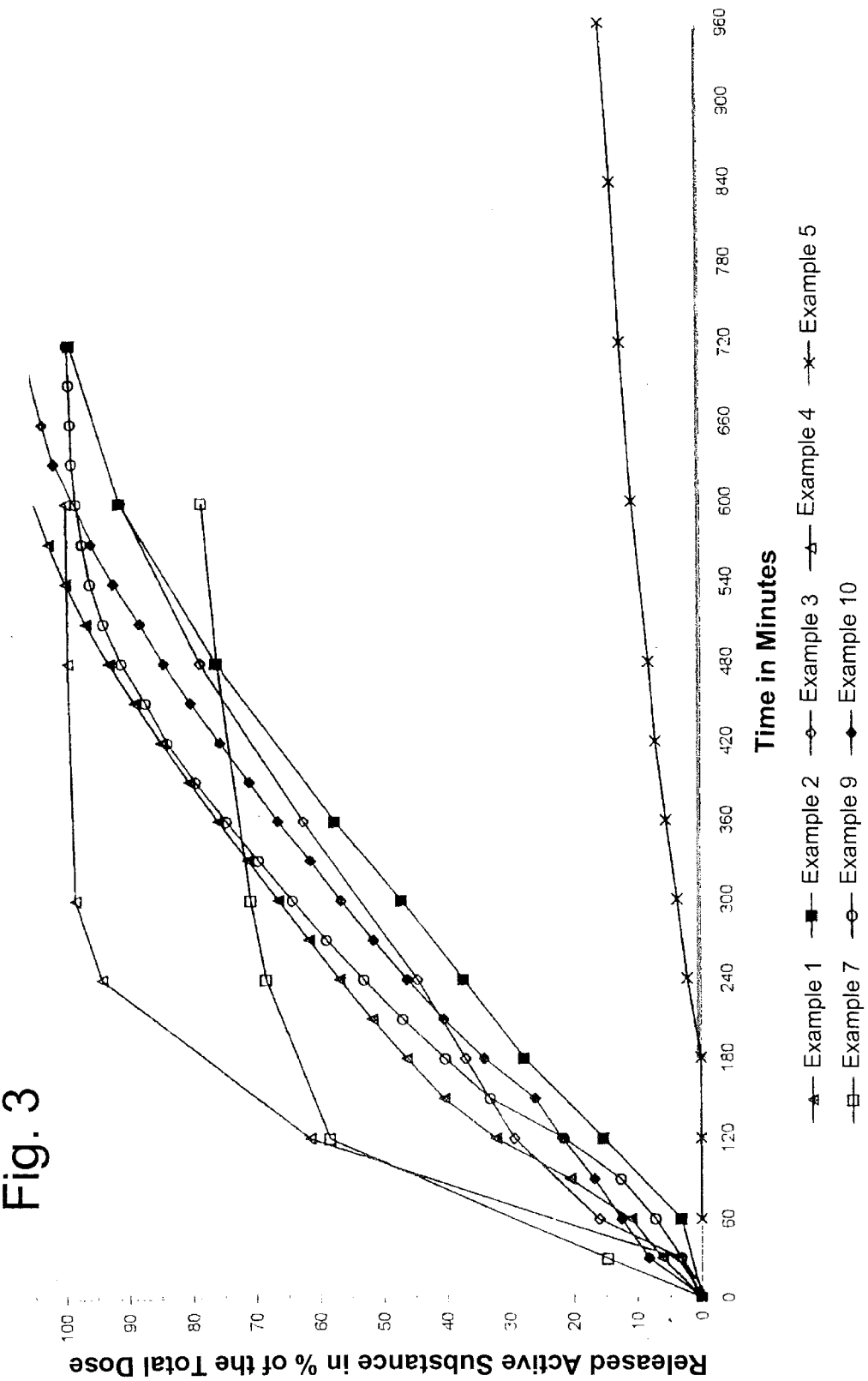

FIG. 3 shows a selection of different profiles for the release of the active substance tramadol saccharinate from extruded pellets which have been coated from aqueous dispersion. Depending on the film composition and the film layer thickness, suitable active substance release profiles can be obtained for formulations to be taken once a day or twice a day, and the release kinetics can be shifted from 1st order to zero order. This shows the great variety of active substance release profiles which can be obtained simply by using commercially available polymer dispersions as recommended by the manufacturer, without further measures or special additives.

The foregoing description and examples have been set forth merely to illustrate invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A pharmaceutical formulation comprising tramadol saccharinate coated with at least one sustained-release coating, and a pharmaceutically acceptable excipient.

2. A pharmaceutical formulation according to claim 1, wherein the tramadol saccharinate is a compound formed in situ.

3. A pharmaceutical formulation according to claim 1, wherein the tramadol saccharinate is a compound prepared using a water-soluble, pharmaceutically acceptable salt of tramadol, and a water-soluble, pharmaceutically acceptable salt of saccharin.

4. A pharmaceutical formulation according to claim 3, wherein the water-soluble, pharmaceutically acceptable salt of tramadol is tramadol hydrochloride.

5. A pharmaceutical formulation according to claim 3, wherein the water-soluble, pharmaceutically acceptable salt of saccharin is a sodium, potassium, calcium or ammonium salt of saccharin.

6. A pharmaceutical formulation according to claim 5, wherein the water-soluble, pharmaceutically acceptable salt of saccharin is a sodium salt of saccharin.

7. A pharmaceutical formulation according to claim 1, which is for oral administration.

8. A pharmaceutical formulation according to claim 7, which is a tablet, a capsule or a suspension.

9. A pharmaceutical formulation according to claim 7, which is a multiparticulate formulation.

10. A pharmaceutical formulation according to claim 9, wherein the formulation in the form of microtablets, microcapsules, micropellets, granules, active substance crystals or pellets.

11. A pharmaceutical formulation according to claim 10, wherein the pharmaceutical formulation is filled into capsules or compressed into tablets, or in a hydrophilic or lipophilic liquid.

12. A pharmaceutical formulation according to claim 10, wherein the granules or pellets have a size in the range of 0.1 to 3 mm.

13. A pharmaceutical formulation according to claim 12, wherein the granules or pellets have a size in the range of 0.5 to 2 mm.

14. A pharmaceutical formulation according to claim 10, wherein the microtablets have a diameter of 0.5 to 5 mm.

15. A pharmaceutical formulation according to claim 14, wherein the microtablets have a diameter of 1 to 3 mm.

16. A pharmaceutical formulation according to claim 15, wherein the microtablets have a diameter of 1 to 2 mm.

17. A pharmaceutical formulation according to claim 10, wherein the active substance crystals, microparticles, micropellets or microcapsules have a diameter of 10 $\mu$m to 1 mm.

18. A pharmaceutical formulation according to claim 17, wherein the active substance crystals, microparticles, micropellets or microcapsules have a diameter of 15 $\mu$m to 0.5 mm.

19. A pharmaceutical formulation according to claim 18, wherein the active substance crystals, microparticles, micropellets or microcapsules have a diameter of 30 $\mu$m to 200 $\mu$m.

20. A pharmaceutical formulation according to claim 1, wherein the sustained-release coating is a coating polymer based on a water-insoluble, modified, natural or synthetic polymer; on a natural, semisynthetic or synthetic wax or fat or fatty alcohol; or on a mixture of at least two of these components.

21. A pharmaceutical formulation according to claim 20, wherein the water-insoluble polymer is a poly(meth)acrylate.

22. A pharmaceutical formulation according to claim 21, wherein the poly(meth)acrylate is a poly($C_{1-4}$)alkyl(meth)acrylate, a poly($C_{1-4}$)dialkylamino($C_{1-4}$)alkyl(meth)acrylates, or a copolymer thereof, or a mixture of at least two of the above-mentioned polymers.

23. A pharmaceutical formulation according to claim 22, wherein the copolymer is selected from the group consisting of an ethyl acrylate/methyl methacrylate copolymer with a monomer molar ratio of 2:1, an ethyl acrylate/methylmethacrylate/trimethylammonium ethyl methacrylate-chloride copolymer with a monomer molar ratio of 1:2:0.1, and an ethyl acrylate/methyl methacrylate/trimethylammonium ethyl methacrylate-chloride copolymer with a monomer molar ratio of 1:2:0.2.

24. A pharmaceutical formulation according to claim 20, wherein the water-insoluble polymer is a cellulose derivative.

25. A pharmaceutical formulation according to claim 24, wherein the cellulose derivative is an alkyl cellulose or a cellulose ester.

26. A pharmaceutical formulation according to claim 25, wherein the alkyl cellulose is ethyl cellulose.

27. A pharmaceutical formulation according to claim 25, wherein the cellulose ester is cellulose acetate.

28. A pharmaceutical formulation according to claim 21, wherein the polymer is applied from an aqueous medium.

29. A pharmaceutical formulation according to claim 28, wherein the aqueous medium is an aqueous latex or pseudolatex dispersion.

30. A pharmaceutical formulation according to claim 20, wherein the coating polymer is a mixture of polyvinyl acetate and polyvinylpyrrolidone.

31. A pharmaceutical formulation according to claim 30, wherein the mixture of polyvinyl acetate and polyvinylpyrrolidone is in the form of an aqueous pseudolatex dispersion.

32. A pharmaceutical formulation according to claim 20, wherein the wax is selected from the group consisting of carnauba wax, beeswax, glycerol monostearate, glycerol monobehenate, glycerol ditripalmitostearate, and microcrystalline wax, or is a mixture of at least two thereof.

33. A pharmaceutical formulation according to claim 20, wherein the wax is applied by a hot-melt coating process.

34. A pharmaceutical formulation according to claim 20, wherein the polymer is combined with a plasticizer.

35. A pharmaceutical formulation according to claim 34, wherein plasticizer is selected from the group consisting of a lipophilic diester of a $C_6$–$C_{40}$ aliphatic or aromatic dicarboxylic acid and a $C_1$–$C_8$ aliphatic alcohol, a hydrophilic or lipophilic citric acid ester, a polyethylene glycol, a propylene glycol, a glycerol ester, and oleic acid, or a mixture of at least two thereof.

36. A pharmaceutical formulation according to claim 35, wherein the lipophilic diester of a $C_6$–$C_{40}$ aliphatic or aromatic dicarboxylic acid and a $C_1$–$C_8$ aliphatic alcohol is dibutyl phthalate, diethyl phthalate, dibutyl sebacate or diethyl sebacate.

37. A pharmaceutical formulation according to claim 35, wherein the a hydrophilic or lipophilic citric acid ester is triethyl citrate, tributyl citrate, acetyltributyl citrate or acetyltriethyl citrate.

38. A pharmaceutical formulation according to claim 35, wherein the glycerol ester is selected from the group consisting of triacetin, acetylated mono- and diglycerides, and a medium-chain triglyceride.

39. A pharmaceutical formulation according to claim 34, wherein the plasticizer is present in amounts of 5 to 50 wt. % based on the polymeric coating material.

40. A pharmaceutical formulation according to claim 39, wherein the plasticizer is present in amounts of 10 to 40 wt. % based on the polymeric coating material.

41. A pharmaceutical formulation according to claim 40, wherein the plasticizer is present in amounts of 10 to 30 wt. % based on the polymeric coating material.

42. A pharmaceutical formulation according to claim 1, further comprising a sustained-release matrix.

43. A pharmaceutical formulation according to claim 42, wherein the sustained-release matrix is based on a hydrophilic polymer.

44. A pharmaceutical formulation according to claim 43, wherein the hydrophilic polymer is at least one selected from the group consisting of a cellulose ether, a cellulose ester, and an acrylic resin.

45. A pharmaceutical formulation according to claim 44, wherein the hydrophilic polymer is at least one selected from the group consisting of ethyl cellulose, hydroxypropyl methyl cellulose, hydroxypropyl cellulose, hydroxymethyl cellulose, a poly(meth)acrylic acid, and a salt, an amide and an ester thereof.

46. A pharmaceutical formulation according to claim 42, wherein the sustained-release matrix is based on a hydrophobic matrix material.

47. A pharmaceutical formulation according to claim 46, wherein the hydrophobic matrix material is a hydrophobic polymer, wax, fat, long-chain fatty acid, fatty alcohol or a corresponding ester or ether, or a mixture thereof.

48. A pharmaceutical formulation according to claim 47, wherein the hydrophobic matrix material is at least one selected from the group consisting of a $C_{12}$–$C_{30}$ fatty acid mono- or diglyceride, a $C_{12}$–$C_{30}$ fatty alcohol, and wax, or a mixture thereof.

49. A pharmaceutical formulation according to claim 1, further comprising an additional coating which is an enteric coating.

50. A pharmaceutical formulation according to claim 49, wherein the enteric coating comprises a methacrylic acid/methyl methacrylate copolymers with a monomer molar ratio of 1:1, a methacrylic acid/methyl methacrylate copolymer with a monomer molar ratio of 1:2, a methacrylic acid/ethyl acrylate copolymer with a monomer molar ratio of 1:1, a methacrylic acid/methyl acrylate/methyl methacrylate with a monomer molar ratio of 7:3:1, shellac, hydroxypropyl methyl cellulose acetate-succinate, cellulose acetate-phthalate or a mixture of at least two thereof.

51. A pharmaceutical formulation according to claim 50, wherein the enteric coating further comprises a poly(meth)acrylate.

52. A pharmaceutical formulation according to claim 51, wherein the poly(meth)acrylate is at least one of an ethyl acrylate/methyl methacrylate copolymer with a monomer molar ratio of 2:1, an ethyl acrylate/methylmethacrylate/trimethylammonium ethyl methacrylate-chloride copolymer with a monomer molar ratio of 1:2:0.1, and an ethyl acrylate/methyl methacrylate/trimethylammonium ethyl methacrylate-chloride copolymer with a monomer molar ratio of 1:2:0.2.

53. A pharmaceutical formulation according to claim 1, further comprising a non-retarded dosage form of tramadol.

54. A pharmaceutical formulation according to claim 1, wherein the tramadol saccarinate has a sustained release profile which is stable on storage without tempering.

55. A pharmaceutical formulation according to claim 1, wherein the sustained-release coating has been applied from aqueous media and not tempered after drying.

56. A pharmaceutical formulation according to claim 1, wherein the formulation is in a once-a-day dosage form containing 10 to 1200 mg of tramadol saccharinate.

57. A pharmaceutical formulation according to claim 56, wherein the formulation is in a once-a-day dosage form containing 20 to 1000 mg of tramadol saccharinate.

58. A pharmaceutical formulation according to claim 57, wherein the formulation is in a once-a-day dosage form containing 100 to 800 mg of tramadol saccharinate.

59. A pharmaceutical formulation according to claim 1, wherein the formulation is in a twice-a-day dosage form containing 5 to 600 mg of tramadol saccharinate.

60. A pharmaceutical formulation according to claim 59, wherein the formulation is in a twice-a-day dosage form containing 10 to 500 mg of tramadol saccharinate.

61. A pharmaceutical formulation according to claim 1, wherein the formulation is in a twice-a-day dosage form containing 50 to 400 mg of tramadol saccharinate.

62. A method for the control or treatment of at least one condition selected from the group consisting of pain, urinary incontinence, coughs, inflammatory reactions, allergic reactions, depression, drug abuse, alcohol abuse, gastritis, diarrhea, cardiovascular disease, respiratory disease, mental illness, and epilepsy, the method comprising administering an effective amount of the pharmaceutical formulation of claim 1 to a patient in need thereof.

* * * * *